United States Patent [19]

Fukuda et al.

[11] Patent Number: 4,627,289

[45] Date of Patent: Dec. 9, 1986

[54] METHOD FOR THE ULTRASONIC FLAW DETECTION OF AN ELECTRIC WELDED PIPE

[75] Inventors: Shinichi Fukuda; Masaki Kajiyama; Takeshi Ikemoto, all of Hikari City, Japan

[73] Assignee: Nippon Steel Corporation, Tokyo, Japan

[21] Appl. No.: 687,425

[22] Filed: Dec. 28, 1984

[30] Foreign Application Priority Data

Nov. 6, 1984 [JP] Japan ................................ 59-232491

[51] Int. Cl.⁴ ............................................. G01N 29/04
[52] U.S. Cl. ........................................ 73/622; 73/638
[58] Field of Search ................. 73/622, 623, 629, 637, 73/638, 640

[56] References Cited

U.S. PATENT DOCUMENTS

| | | | |
|---|---|---|---|
| 3,302,453 | 2/1967 | Wood et al. | 73/622 |
| 4,375,165 | 3/1983 | deSterke | 73/637 |
| 4,406,167 | 9/1983 | Maeda | 73/622 |
| 4,531,409 | 7/1985 | Koch et al. | 73/622 |

*Primary Examiner*—Howard A. Birmiel
*Attorney, Agent, or Firm*—Wenderoth, Lind & Ponack

[57] ABSTRACT

An ultrasonic flaw detection method in which defects in the weld zone of an electric resistance welded steel pipe are detected by projecting an ultrasonic wave (a) having a frequency range of from 25 MHz to 500 MHz at an angle of incidence of from 0° to 12° onto the weld zone of the pipe. In addition by projecting another ultrasonic wave (b) having a frequency of from 2 MHz to 10 MHz at an angle of incidence of from 15° to 27° onto the same weld zone enables discrimination between cold weld defects and other defects such as inclusions and penetrators.

3 Claims, 13 Drawing Figures

METHOD FOR THE ULTRASONIC FLAW DETECTION OF AN ELECTRIC WELDED PIPE

BACKGROUND OF THE INVENTION

1. Field of the Invention

The present invention relates to a method for the ultrasonic detection of cold weld defects occurring at the weld zone in seam welded pipe.

2. Description of the Prior Art

Figure 1:
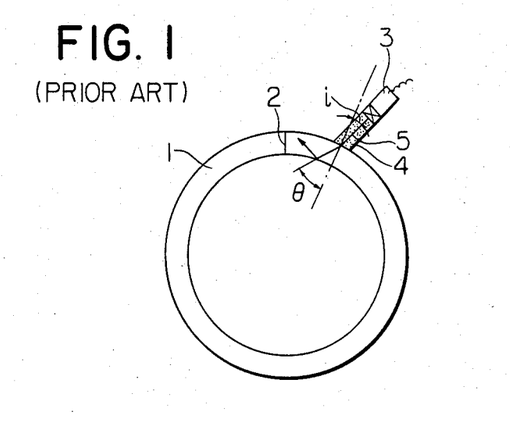
FIG. 1 is schematic view explaining a conventional circumferential angle beam flaw inspection where the probe is positioned away from the weld zone and the ultrasonic beam is reflected at the surfaces of the pipe.

In general, the conventional ultrasonic flaw detection method used for electric welded steel pipe has been the circumferential angle beam technique illustrated in FIG. 1 of the accompanying drawings. In FIG. 1, an ultrasonic beam 5 transmitted from a probe 3 is projected through water 4 into a pipe 1 at an angle of incidence i and is refracted at an angle $\theta$. Any defect encountered in the pipe by the ultrasonic beam will reflect the beam back along the same path to be received by the probe 3.

The frequency f of the signal from the probe in the above circumferential angle beam technique usually has been set at 2.25 MHz to 5 MHz and a refractive angle $\theta$ of 37° to 90° has been used for detecting a flaw in the weld zone 2 of the pipe. In the case of steel pipe, if the angle of incidence i is set at 16.0° to 27.3°, the refractive angle $\theta$ will fall within the above mentioned range. Further, in order to attain certain detection of flaws in the weld zone 2, electromagnetic induction systems, optical systems, paint mark systems, magnetic mark systems, and visual systems, and the like are used to ensure that the probe 3 follows the weld zone 2 during the detection. Furthermore, plural numbers of probes 3 are positioned with a set interval between each probe for maintaining the accuracy of the detection and tracking.

Figure 2:
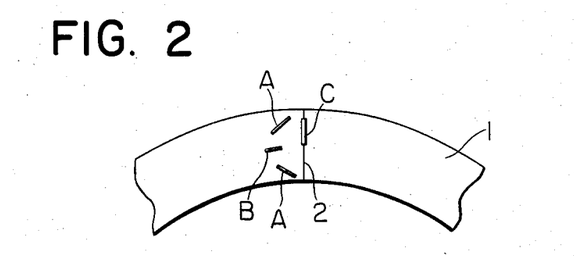
FIG. 2 is a schematic view explaining defects which exist in the electric resistance welded steel pipe.

In ultrasonic flaw inspection in accordance with the conventional methods, penetrators existing in the weld zone 2 can be detected with certainty. Moreover, as shown in FIG. 2, because not only the weld zone 2 but also the parent metal in the proximity of the weld zone are subjected to the ultrasonic beam, the penetrator C in the weld zone 2 together with inclusions A and B, which cause little harm, can be detected. However, cold weld defects, existing in the weld zone of the electric welded steel pipe are not detected.

The cold weld defects which are produced when the welding heat input is low, are very fine oxides no larger than several microns, and consist mainly of FeO. Those oxides form an aggregation at the weld zone. The presence of a cold weld defect in the weld zone results in considerable reduction in the toughness of the pipe. It is known that the above cold weld defects are undetectable using conventional ultrasonic flaw inspection methods of the prior art or any other non-destructive testing method (W. Stumm: Magnetic stray-flux measurement for testing welded tubes on line, Non-destructive Testing, Vol. 9, No. 1 (1976), Pages 3-8).

Accordingly, the presence of cold weld defects has been discerned by other inspection methods, such as carrying out a rupture test via by fatigue test or a Charpy impact test conducted on samples, and then by observing the face of the fracture with a microscope.

SUMMARY OF THE INVENTION

It is an object of the present invention to provide an ultrasonic flaw inspection method for cold weld defects in the weld zone of electric resistance welded pipe.

It is another object of the invention to provide an ultrasonic flaw detection method by which the quality of the weld zone of electric resistance welded pipe can be guaranteed.

BRIEF DESCRIPTION OF THE DRAWINGS

Other and further objects of the invention will become apparent to those skilled in the art from the following detailed description of the invention with reference to the drawings which illustrate a preferred embodiment of the invention.

DETAILED DESCRIPTION OF THE INVENTION

Figure 3:
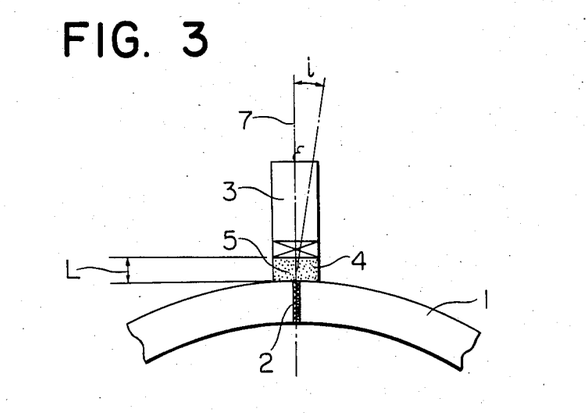
FIG. 3 is a view showing the arrangement of a probe and a pipe in the inspection method for cold weld defects in accordance with the present invention.
Figure 4:
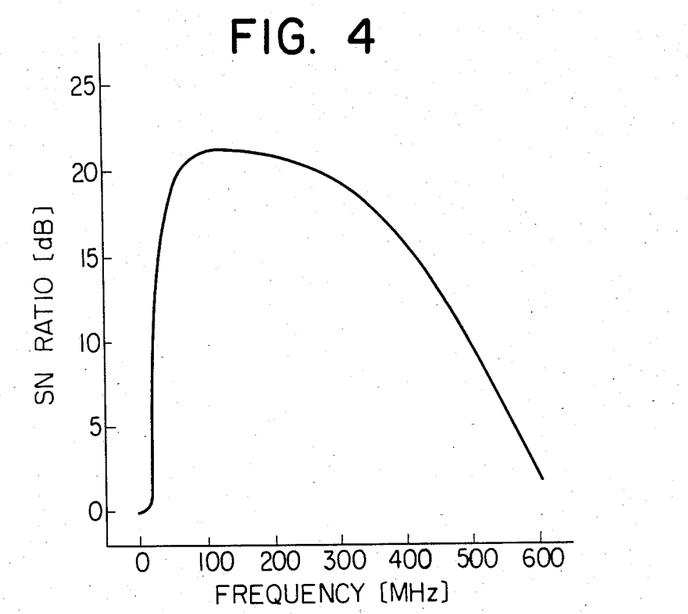
FIG. 4 is a graph showing the detection characteristics of the cold weld defects with a change in the frequency of the ultrasonic wave applied according to the method of the present invention.

After various experimental research, the inventors of the present invention discovered that a reflected echo with a high signal-to-noise ratio (hereinafter referred to as "SN ratio") can be reflected from a very fine cold weld defect by scanning the weld zone by a pulse reflection method with a single probe and by using a high test frequency for the ultrasonic wave. As shown in FIG. 3, a probe 3 is set in a direction of the normal 7 to a tangent to the outer surface of the electric welded pipe 1, and an ultrasonic beam 5 is projected perpendicularly from the outer surface of the weld zone 2 in the direction of the thickness of the pipe wall. Using an ultrasonic beam with a frequency f of from 2.25 MHz to 600 MHz, the magnitude of the reflected echo from a cold weld defect and of the noise is as shown in FIG. 4.

It is seen that with an ultrasonic wave of a frequency f of less than 20 MHz there is hardly any echo from the cold weld defect. For a frequency of 25 MHz or more to not more than 500 MHz, the SN ratio is more than 10 dB; and with an ultrasonic wave of a frequency of 600 MHz there is again hardly any echo from the cold weld defect.

In addition, the probe 3 was positioned so as to project an ultrasonic wave beam 5 of a frequency of 50 MHz at the angle of inclination i (hereinafter referred to as the angle of incidence i) in the range of 0° to 20° from the normal 7 to a tangent to the outer surface of the electric resistance welded pipe 1 in FIG. 3, to examine the magnitudes of the reflected echo and of the noise.

Figure 5:
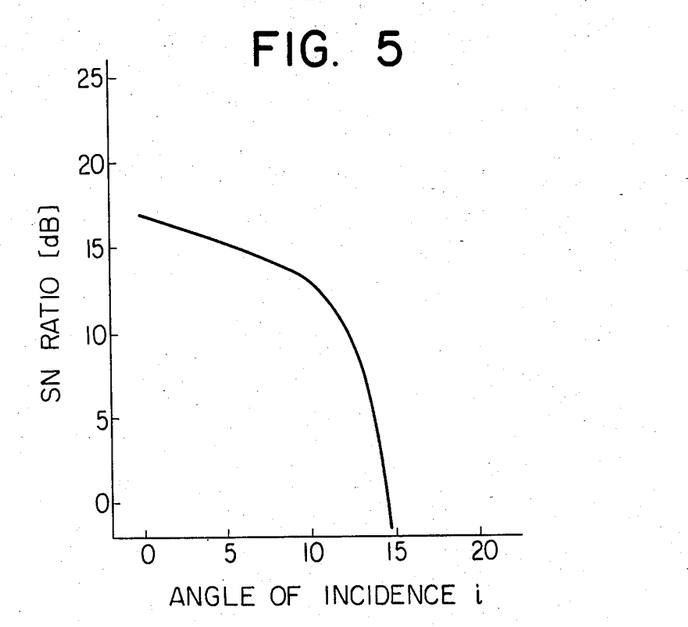
FIG. 5 is a graph showing the detection characteristics of the cold weld defects with a change in the angle of incidence of the ultrasonic wave applied according to the method of the present invention.

The results are indicated in FIG. 5, and it shows that the SN ratio is 10 dB or more if the angle of incidence i is in the range of 0°-12°, and that cold weld defects can thus be satisfactorily detected. If the SN ratio is 10 dB or more, the automatic ultrasonic flaw detection can be carried out as stably as with the conventional circumferential angle beam technique. Therefore, if the resolving power and the SN ratio are taken into consideration, it is seen that cold weld defects can be detected reliably by applying an ultrasonic wave having a frequency f in the range of 25 MHz to 500 MHz, and by projecting the ultrasonic wave at an angle of incidence i in the range of 0° to 12° to the normal to the tangent to the pipe at the position of the weld.

In addition to the above-mentioned cold weld defect, other flaws in the weld zone which can be detected include flaws consisting of oxide inclusion of Fe, Al, or Ca of not more than about 10 microns in size, and slight penetrators.

Furthermore, the inventors also discovered from experiments that the reflected echo with a high SN ratio can be obtained from very fine cold weld defects, and that penetrators and inclusions in the proximity of the weld zone can also be detected by means of the high frequency single probe pulse reflection method, and that detection of those penetrators and inclusions can at the same time be attained by substantially simultaneously carrying out a low frequency single probe pulse reflection method.

Figure 6:
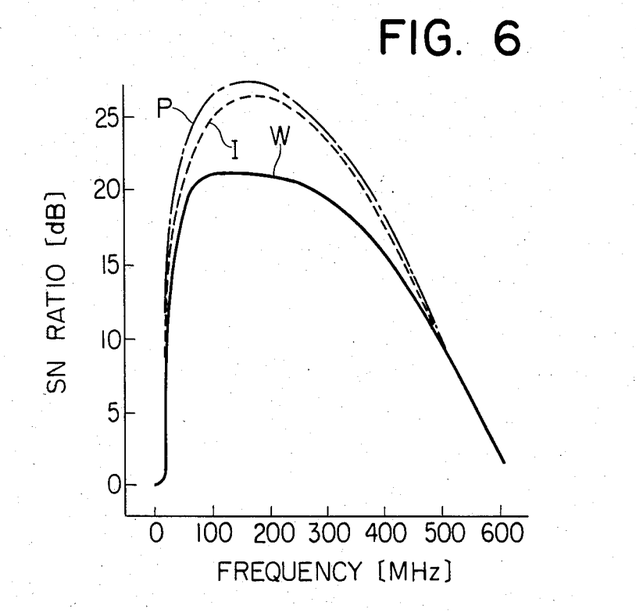
FIG. 6 is a graph showing the detection characteristics of defects in a high frequency region of the ultrasonic wave applied according to the method of the present invention.

As indicated in FIG. 3, the probe 3 is positioned along the direction of the normal to a tangent to the outer surface of the electric welded pipe 1, and the ultrasonic wave beam 5 is perpendicularly projected from the outer surface immediately above the weld zone 2 in the direction of the wall thickness. After applying an ultrasonic wave having a frequency f of 2.25 MHz to 600 MHz, the magnitudes of a reflected echo and of the noise resulting from the cold weld defects penetrators, and inclusions were examined. The results are shown in FIG. 6.

For a cold weld defect W, there are almost no echoes of the ultrasonic wave of a frequency of 20 MHz or less, but an ultrasonic wave of a frequency of 25 MHz to 500 MHz is echoed back with SN ratio of more than 10 dB. With an ultrasonic wave of 600 MHz, hardly any echoes are produced.

As regards the penetrators P and inclusions I, with the ultrasonic wave of a frequency f of 15 MHz or less, hardly any echoes are produced, while an ultrasonic wave of 20 MHz to 500 MHz results in an SN ratio of 10 dB or more. With an ultrasonic wave of 600 MHz hardly any echoes are produced.

Figure 7:
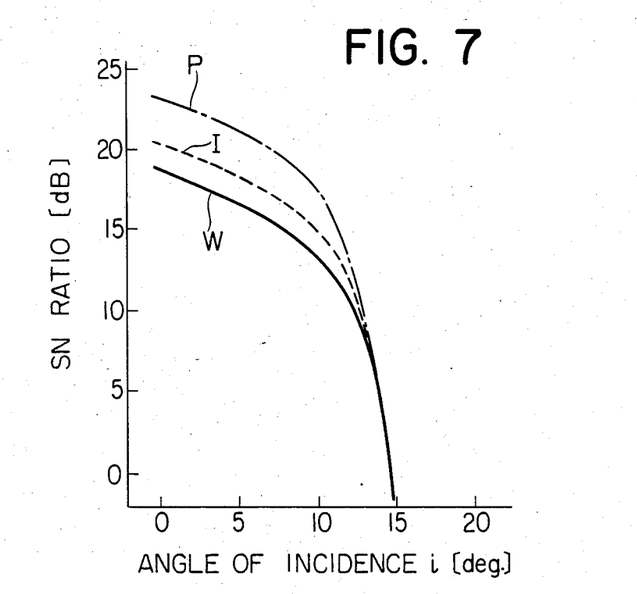
FIG. 7 is a graph showing the detection characteristics of defects with a change in the angle of incidence of the ultrasonic wave applied.

In FIG. 3, the frequency f of the ultrasonic wave was set at 50 MHz, and the probe 3 was so positioned that the ultrasonic wave beam 5 could be projected into the electric welded pipe 1 at an angle of incidence in the range 0°-20°, and the magnitudes of the reflected echo and of the noise returned by cold weld defects. Penetrators, and inclusions were examined. The results are shown in FIG. 7.

It has been discovered that at an angle of incidence i in the range 0°-12° the SN ratio was 10 dB or more, allowing cold weld defects W, penetrators P, and inclusions I to be detected. Accordingly, in consideration of the resolving power and the SN ratio, penetrators and inclusions are detected, and cold weld defects can also be certainly detected as well by the method of this invention in which an ultrasonic wave with a frequency f of 25 MHz to 500 MHz is projected into the weld zone of a steel pipe at an angle of incidence i in the range 0°-12° to a normal to a tangent to the pipe at the position of the weld.

Figure 8:
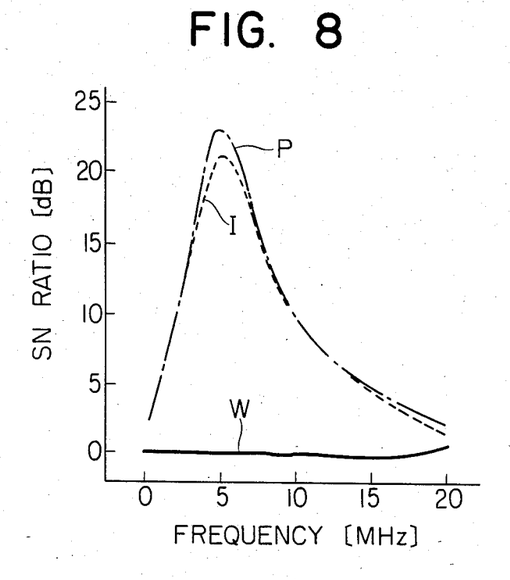
FIG. 8 is a graph showing the detection characteristics of the defects in the low frequency region of the ultrasonic wave applied according to the prior art method.

In FIG. 1, the probe 3 was positioned at an angle of incidence i of 19°, for obliquely projecting the ultrasonic beam 5 into the outer surface of the electric welded pipe. An ultrasonic wave frequency of 0.5 to 20 MHz was used, and the magnitudes of the reflected echo and the noise returned by the cold weld defects, penetrators, and inclusions were investigated. The results are shown in FIG. 8.

With reference to the cold weld defect W, hardly any echo of the ultrasonic wave of any frequency was obtained. As regards the penetrators P and inclusions I, an ultrasonic wave 1 MHz or less in frequency showed hardly any reflection; but when the frequency was in the range 2 MHz to 10 MHz, the beam reflected at an SN ratio of 10 dB or more. It is seen that there was hardly any echo of an ultrasonic beam of 15 MHz or more.

Figure 9:
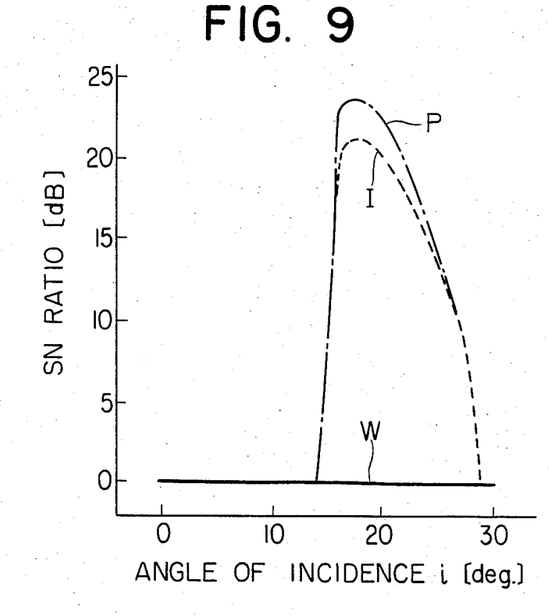
FIG. 9 is a graph illustrating the detection characteristics of the defects with a change in the angle of incidence of the ultrasonic wave in the low frequency region of the ultrasonic wave applied according to the prior art method.

Furthermore, the ultrasonic wave beam was projected into the weld zone of the pipe with the probe 3 of FIG. 1 using an ultrasonic wave of a frequency f of 5 MHz and positioned at an angle of incidence i of 0°-30°. The results of the examination of cold weld defects, penetrators, and inclusions are shown in FIG. 9 which indicates the magnitudes of the reflected echo as well as of the noise.

At any angle of incidence, with respect to the cold weld defects, the ultrasonic wave is hardly reflected at all.

Regarding penetrators P and inclusions I, there is almost a complete absence of ultrasonic beam reflection at angles of incidence of 14° or less and 28° or more, whereas the beam is reflected at an SN ratio of 10 dB or more when the angle of incidence is from 15° to 27°. When the resolving power and the SN ratio are taken into consideration, penetrators and inclusions can be detected with certainty by projecting the ultrasonic wave at an angle of incidence from 15° to 27°.

As described hereinbefore, it is seen that cold weld defects, penetrators, and inclusions can be detected using an ultrasonic wave frequency of 25 MHz to 500 MHz (hereinafter referred to as high frequency ultrasonic waves), and penetrators and inclusions can also be detected using an ultrasonic wave of 2 MHz to 10 MHz (hereinafter referred to as low frequency ultrasonic waves). Based on the above findings, it follows that a defect which can be detected by a high frequency ultrasonic wave but not by a low frequency ultrasonic wave, can be regarded as being a cold weld defect.

As described in the foregoing, in accordance with the ultrasonic flaw inspection method of the present invention for the weld zone of the electric welded steel pipe, without sacrificing detection of penetrators and inclusions, it is possible to detect with certainty cold weld defects, which was hitherto impossible using a conventional non-destructive testing method.

Accordingly, it contributes much to the testing of a tubular material intended for rigorous services in a cryogenic environment, and moreover, the quality of the electric welded steel pipe can be guaranteed. Thus, use of electric seam welded steel pipe can become feasible in fields heretofore requiring use of seamless pipe.

Embodiments of the present invention are described hereinbelow.

Example 1

Figure 10:
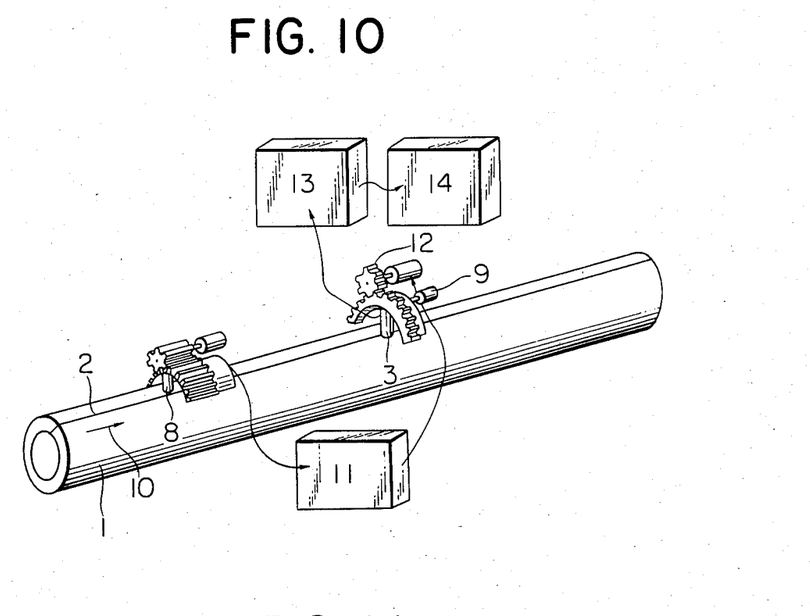
FIG. 10 is a block diagram showing an arrangement of means for carrying out an embodiment of the invention.

Table 1 shows electric resistance seam welded pipes made of carbon steel which were welded under a heat weld input such that a cold weld defect was most likely brought about. FIG. 10 depicts an arrangement for the means for carrying out the present invention. As indicated in FIG. 10, an angle of incidence i of 0°, was used for a detector 8 of an ordinary electromagnetic induction system in order to detect the seam position of the welded zone 2 exactly. A probe 3 was arranged to follow the weld zone by a tracking controller 11 and a tracking means 12. For flaw detection and tracking accuracy, the probe 3 was caused to oscillate circumferentially by an oscillating motor 9 so as to be able to detect both sides of the weld zone 2 in the range of 10 mm. In FIG. 10, arrow 10 shows the direction of pipe movement, 13 designates an ultrasonic flaw inspecting apparatus, and 14 designates a recorder.

In the above case, the frequency f of the probe 3 was 50 MHz, the size of the transducer was 0.250 in.$\phi$, and a point-focus type was used with a focal distance of 0.5 in. The distance for flaw detection (FIG. 3) was set at 3 mm, and an inspection speed V of 10 m/min. was used for the flaw detection.

With reference to the conventional ultrasonic flaw inspection method, the frequency f was 5 MHz, the size d of the transducer was 10 mm$\phi$, the probe was a flat type having a focal distance of 60 mm, and the refractive angle $\theta$ was 45°. Other flaw detection conditions were the same as those described for the embodiment of the present invention.

TABLE 1

| Sample No. | Outside diameter D (mm$\phi$) | Wall thickness t (mm) | Detection Results SN ratio (dB) | |
|---|---|---|---|---|
| | | | Present Invention | Prior Art |
| 1 | 48.6 | 3.0 | 21.2 | 0 |
| 2 | 60.5 | 4.5 | 20.0 | 0 |
| 3 | 76.3 | 5.0 | 20.8 | 0 |
| 4 | 114.3 | 6.0 | 19.5 | 0 |
| 5 | 406.4 | 12.5 | 20.6 | 0 |
| 6 | 457.2 | 9.5 | 18.5 | 0 |
| 7 | 508.0 | 16.0 | 14.9 | 0 |
| 8 | 609.6 | 12.5 | 17.5 | 0 |

TABLE 1-continued

Figure 11:
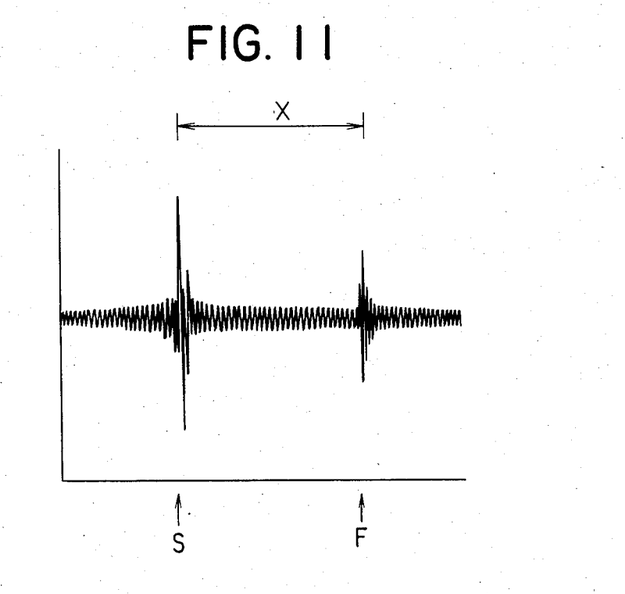
FIG. 11 is a reproduction of a wave form displayed on a cathode. ray tube showing the results of a defect detection carried out by the means of FIG. 10.

As clearly shown in the results listed in Table 1, it is impossible for the conventional method of the prior art to detect cold weld defects, but in accordance with the method of the present invention, all the flaws in the weld zone of the tubular material can be detected with an SN ratio of more than 10 dB. FIG. 11 depicts, for instance, a model pattern displayed on a cathode ray tube obtained from the flaw detection in connection with Sample No. 5 of Table 1; the echo is reflected from a cold weld defect perceived at the position (X) 9.7 mm from the outer surface of the tubular material. S is a surface echo and F is the cold weld defect echo.

Example 2

Figure 12:
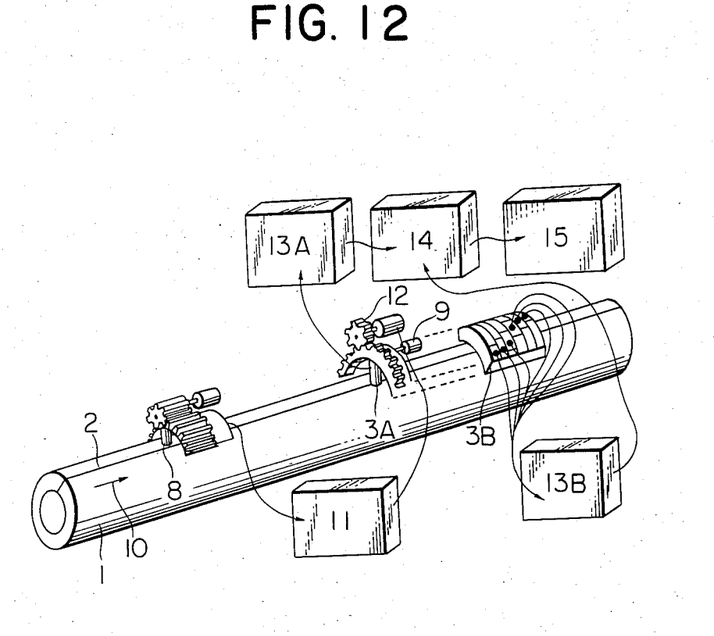
FIG. 12 is a block diagram showing the arrangement of another means for carrying out another embodiment of the invention.

As indicated in Table 2, electric resistance welded carbon steel pipes of various outer diameters and wall thicknesses were used as samples. The pipes used were such as could contain inclusions, cold weld defects and penetrators. All of the samples were welded under a heat input such that the cold weld defects or penetrators were most likely brought about. FIG. 12 illustrates an arrangement of means to carry out the present invention.

A high frequency probe 3A was set at an angle of incidence i of 0°, and the angle of incidence i of a low frequency probe 3B was set at 19°. As shown in FIG. 12, in order to surely detect flaws in the weld zone 2 of the pipe, the weld zone 2 was detected by a detector 8 of an ordinary electromagnetic induction system, and the probeds 3A and 3B were arranged to trace or be guided along the weld zone by a tracking controller 11 and a tracking means 12. In consideration of the detection and tracking accuracy, the probe 3A was caused to oscillate circumferentially by an oscillating motor 9, and probes 3B were provided at set intervals. Detection was carried out at both sides of the weld zone 2 in the range of 10 mm respectively.

Defect signals picked up by probes 3A and 3B were discriminated by a discriminator 14, and it was arranged that defects indicated by defect signals from the high frequency probe 3A only would be marked in white paint and defects indicated by defect signals from the low frequency probe 3B would be marked in yellow. In FIG. 10, arrow 10 shows the direction of pipe movement, 13A and 13B designate the ultrasonic flaw detectors and 15 designates a recorder.

In Example 2, the frequency f of the probe 3A was 25 MHz or 500 MHz, the size d of the transducer was 0.250 in.$\phi$, the focal distance F of the point focus type was 0.5 in., the distance L for flaw detection (FIG. 3) was 3 mm, and the angle of incidence i was 12°. An inspecting speed V of 10 m/min. was used for the flaw detection. The frequency of the probe 3B was set at 2 MHz and 10 MHz, the size d of the transducer of the flat type was 10 mm, the distance L for flaw detection was 40 mm, and the angle of incidence was 15° and 27°; an inspecting speed V of 10 m/min. was used. In addition, the probe 3B was set under the same conditions as that of the conventional method of the prior art, and it was compared with that of the present invention. Furthermore, a cutting test was used to examine defects detected with the conventional method as well as with the present invention.

TABLE 2

| Sample No. | Outer diameter (mmφ) | Wall thickness (mmt) | Probe 3A Frequency (MHZ) | Probe 3A Angle of incidence (deg.) | Probe 3B Frequency (MHZ) | Probe 3B Angle of incidence (deg.) | Results of Flaw Detection This invention | Results of Flaw Detection Prior art | Results of Cutting Test |
|---|---|---|---|---|---|---|---|---|---|
| 9 | 406.0 | 12.5 | 25 | 12 | 2 | 15 | O | X | Cold weld defect |
| 10 | " | " | " | " | " | " | X | O | Penetrator |
| 11 | " | " | " | " | " | " | X | O | Inclusion |
| 12 | " | " | " | " | 10 | " | O | X | Cold weld defect |
| 13 | " | " | " | " | " | " | X | O | Penetrator |
| 14 | " | " | " | " | " | " | X | O | Inclusion |
| 15 | " | " | " | " | 2 | 27 | O | X | Cold weld defect |
| 16 | " | " | " | " | " | " | X | O | Penetrator |
| 17 | " | " | " | " | " | " | X | O | Inclusion |
| 18 | " | " | " | " | 10 | " | O | X | Cold weld defect |
| 19 | " | " | " | " | " | " | X | O | Penetrator |
| 20 | " | " | " | " | " | " | X | O | Inclusion |
| 21 | " | " | 500 | " | 2 | 15 | O | X | Cold weld defect |
| 22 | " | " | " | " | " | " | X | O | Penetrator |
| 23 | " | " | " | " | " | " | X | O | Inclusion |
| 24 | " | " | " | " | 10 | " | O | X | Cold weld defect |
| 25 | " | " | " | " | " | " | X | O | Penetrator |
| 26 | " | " | " | " | " | " | X | O | Inclusion |
| 27 | " | " | " | " | 2 | 27 | O | X | Cold weld defect |
| 28 | " | " | " | " | " | " | X | O | Penetrator |
| 29 | " | " | " | " | " | " | X | O | Inclusion |
| 30 | " | " | " | " | 10 | " | O | X | Cold weld defect |
| 31 | " | " | " | " | " | " | X | O | Penetrator |
| 32 | " | " | " | " | " | " | X | O | Inclusion |

O . . . Detectable
X . . . Non detectable

Figure 13:
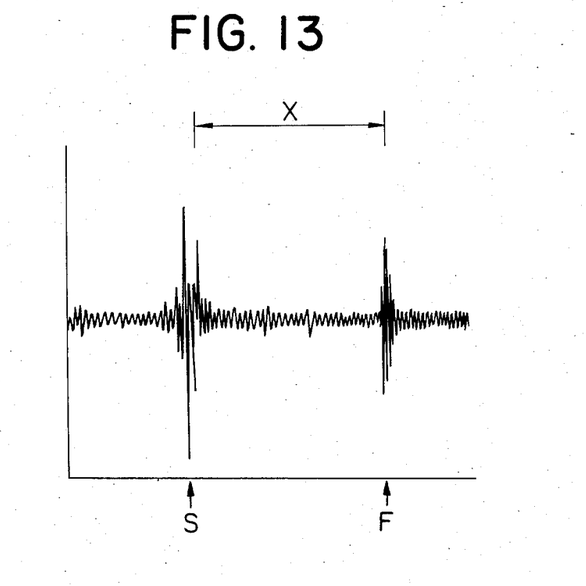
FIG. 13 is a reproduction of a wave form displayed on a cathode ray tube showing the results of the flaw inspection carried out by the means of FIG. 12.

As shown in the results in Table 2, cold weld defects cannot be detected by the conventional flaw detecting method of the prior art but can be detected by the flaw inspecting method according to the present invention, whereas the cold weld defects can be discriminated from the inclusions and penetrators by the method of the present invention. FIG. 13 depicts a model pattern displayed on a cathode ray tube concerning the results of flaw detection inspection of sample No. 21 of Table 2. The reflection indicates a cold weld defect 2.6 mm (X) below the outer surface of the pipe.

The above embodiments are described in connection with electric resistance seam welded carbon steel pipe, but it has been found that the weld zones of any metallic pipe including low alloy steel, stainless steel, and in addition, non-ferrous metal can be detected by the present invention as well. It can also be applied to a square pipe.

We claim:

1. A method for ultrasonic flaw detection of flaws in the weld zone of an electric resistance welded pipe, comprising:

projecting an ultrasonic wave beam having a frequency in the range of 25 MHz to 500 MHz onto the outer surface of said weld zone at an angle of incidence to a perpendicular to the tangent to said pipe at the weld zone, which angle is between 0° and 12°, whereby cold weld defects, inclusions and penetrators in the weld zone are detected.

2. A method as claimed in claim 1 in which said wave beam is projected by a probe, and said probe is moved so as to scan back and forth across said weld zone in a distance range of 10 mm on each side of said weld zone.

3. A method as claimed in claim 1 further comprising projecting an ultrasonic wave beam having a frequency in the range of 2 MHz to 10 MHz onto the outer surface of said weld zone at an angle of incidence to said perpendicular which is between 15° and 27° for detecting inclusions and penetrators, and discriminating signals produced as a result of the projection of the respective wave beams for determining from the signal resulting from the firstmentioned wave beam which of the flaws detected thereby are cold weld defects.

* * * * *